United States Patent [19]
van Veggel et al.

[11] Patent Number: 5,657,156
[45] Date of Patent: *Aug. 12, 1997

[54] POLYMERIC OPTICAL AMPLIFIER DOPED WITH LANTHANIDE

[75] Inventors: Franciscus Cornelis Jacobus Maria van Veggel, LA Hengelo; Gustaaf Ronald Mohlmann, CL Dieren, both of Netherlands

[73] Assignee: Akzo Nobel nv, Arnhem, Netherlands

[*] Notice: The term of this patent shall not extend beyond the expiration date of Pat. No. 5,581,398.

[21] Appl. No.: 615,482

[22] Filed: Mar. 15, 1996

Related U.S. Application Data

[63] Continuation-in-part of Ser. No. 256,035, Aug. 19, 1994, Pat. No. 5,581,398.

[51] Int. Cl.$^6$ .................. H01S 3/00; C07D 321/00
[52] U.S. Cl. .................. 359/342; 549/348; 549/352; 549/353; 436/79; 436/74
[58] Field of Search .................. 359/342, 343, 359/341; 372/39, 40, 41; 549/352, 353; 435/74, 79

[56] References Cited

U.S. PATENT DOCUMENTS

| | | | |
|---|---|---|---|
| 3,949,319 | 4/1976 | Tofield et al. | 331/94.5 |
| 4,476,007 | 10/1984 | Toner et al. | 204/417 |
| 5,177,221 | 1/1993 | Cram et al. | 549/348 |
| 5,383,463 | 1/1995 | Kleinerman | 385/123 |
| 5,485,480 | 1/1996 | Kleinerman | 312/6 |
| 5,490,010 | 2/1996 | Sharma et al. | 359/341 |

FOREIGN PATENT DOCUMENTS 437935  7/1991  European Pat. Off. .......... H01S 3/06

OTHER PUBLICATIONS

"Extraction", Kirk-Othmer's Encyclopedia of Chemical Technology, Third Edition, vol. 10, pp. 125-180.
G.R. Möhlmann et al., "Side Chain Liquid Crystal Polymers as Optically Nonlinear Media", in Side Chain Liquid Crystal Polymers, C.B. McArdle, ed., Chapter 12, pp. 330-356.
K.E. Koenig et al., "Host-Guest Complexation. 16. Synthesis and Cation Binding Characteristics of Macrocyclic Polyethers Containing Convergent Methoxyaryl Groups", J. Amer. Chem. Soc. (1979), vol. 101, pp. 3553-3566.

*Primary Examiner*—Mark Hellner
*Attorney, Agent, or Firm*—Richard P. Fennelly; Louis A. Morris

[57] ABSTRACT

The invention relates to a polymeric optical amplifier doped with lanthanide ions, which are present in the amplifier in the form of a complex.

The invention also relates to novel electrically neutral lanthanide complexes which can be applied with advantage in the above-described polymeric optical amplifiers. These complexes comprise host molecules which readily complex with the lanthanide and fully encapsulate it.

7 Claims, 1 Drawing Sheet

POLYMERIC OPTICAL AMPLIFIER DOPED WITH LANTHANIDE

RELATED APPLICATIONS

This is a continuation-in-part application of U.S. Ser. No. 08/256,035, filed Aug. 19, 1994 now U.S. Pat. No. 5,581,398.

FIELD OF INVENTION

The invention relates to an optical amplifier doped with lanthanide ions. Such an optical amplifier is known from EP-A2-0 437 935, which describes an optical amplifier composed of an erbium$^{3+}$ doped fibre. The erbium ions are excited with the aid of a laser, giving a fibre containing a large number of excited $Er^{3+}$ ions. When optical beams (photons) having the same wavelength as the emission wavelength of the excited $Er^{3+}$ ions traverse the fibre, they effect the transition of the ions from the excited state to a lower energy level with transmission of light. As has been mentioned, this light will have the same wavelength and phase as the photons traversing the fibre. Such a process is called stimulated emission. In this way the light beams are amplified, with the optical fibre acting as amplifier.

DESCRIPTION RELATIVE TO THE PRIOR ART

The optical amplifier as specified in EP-A2-0 437 935 is a glass fibre. For several years efforts have been made in the industry to replace optical glass fibres with optical polymeric material. Optical polymeric fibres have several advantages over optical glass fibres. They can be made by less complicated spinning processes and can easily be cut to the required size and attached to receiving and transmitting devices. Also, they are lighter and more flexible than glass fibres. An attendant advantage is that the shape of optical polymeric material need not be restricted to fibres. The polymeric material can also be shaped into so-called planar waveguides. In the remainder of the description the term optical waveguides refers to both fibres and planar waveguides.

So far, it has not proved possible to replace lanthanide doped optical amplifiers with optical amplifiers of polymeric material. This is because polymeric waveguides cannot be doped with lanthanides just like that, without introducing co-doping with water. For, trivalent lanthanide ions are highly hygroscopic. In consequence, when lanthanide ions are doped, water of crystallisation which is present on the lanthanide salt is also introduced into the waveguide. Alternatively, lanthanide ions already present in the waveguide may interact with water or other OH-containing impurities. Water and other OH-containing impurities quench the excited state of the trivalent lanthanide ions. So, unless further steps are taken, a lanthanide doped optical polymeric waveguide will not have the above-indicated amplification, or have it in insufficient degree. Furthermore, light is absorbed to such an extent by OH-groups that polymeric optical waveguides in which OH-impurities are present will display optical attenuation. Doping of $Er^{3+}$ ions in glass fibres ordinarily is carried out using $Er_2O_3$. While this erbium oxide is not hygroscopic, it cannot be used in polymeric waveguides since it fails to dissolve in polymeric material. When glass fibres contain water or OH-containing impurities, these can easily be removed by greatly heating the fibres and drying them out, as it were. However, this is an unfortunate solution to the problem where polymeric waveguides are concerned, as they will usually decompose under such treatment.

OBJECT OF THE INVENTION

The present invention has for its object to obviate these drawbacks and provide a functional lanthanide doped optical amplifier in which a polymeric waveguide is used as optical material. The invention hence consists in that the polymeric waveguide comprises the lanthanide ions in the form of a complex.

The term complex in this connection refers to a compound in which the lanthanide ion is encapsulated by a host molecule. If a complex is provided in which trivalent lanthanide is fully encapsulated, the lanthanide ions are not, or at any rate less in a position to interact with water or other OH-containing impurities. Moreover, it appears that any water present when such a complex is formed is stripped off the lanthanide. A further advantage of such a lanthanide complex is that it dissolves or mixes with the polymeric material far more readily than lanthanide salts or lanthanide oxides do. This is because like the polymeric waveguide, the host molecule comprises organic material. Hence, it is possible for the lanthanide to be incorporated into a polymeric optical fibre in a permanently anhydrous state in the form of a complex, without the advantages of polymeric optical fibres over glass fibres being attacked. In this way a lanthanide doped polymeric optical amplifier is provided which has all the above-mentioned advantages of polymeric optical waveguides to boot.

All lanthanide ions can be incorporated into polymeric optical waveguides in the form of a complex. Notably suitable are praseodymium (Pr), neodymium (Nd), europium (Eu), terbium (Tb), erbium (Er), thulium (Tm), and ytterbium (Yb). For instance, an optical waveguide into which $Pr^{3+}$ and/or $Nd^{3+}$ is incorporated in the complexed form is suitable for amplifying light of a wavelength of 1,3 micrometers. An optical waveguide into which $Er^{3+}$ is incorporated in the complexed form can be used to amplify light of a wavelength of 1,5 micrometers. Light beams of these wavelengths (1,3 and 1,5 micrometers) are used in telecommunications systems because losses of signal in this wavelength range are minimal. (This wavelength range is a so-called optical window). Optical amplifiers doped with $Eu^{3+}$ can be used for the amplification of red light, while optical amplifiers doped with $Tb^{3+}$ serve to amplify green light.

When optical lanthanide doped waveguides are co-doped with $Yb^{3+}$, the ytterbium ion is excited. This excited $Y^{3+}$ ion can transfer its energy to the lanthanide ion, which will be excited in its turn. Such a transfer of energy can also take place in the case of co-doping with $Pr^{3+}$, $Ne^{3+}$, and $Tm^{3+}$. The advantage here is that, since these lanthanides have absorption bands at different wavelengths, the selection of the type of laser to be used in the exciting process becomes less subject to restriction. $Tm^{3+}$, for instance, has an absorption band at 810 nanometers and so can be excited with a solid-state laser, while for $Er^{3+}$ a different type of laser would be required. The ytterbium ion has a strong absorption band at 1000 nanometers, rendering it more readily excitable than, say, the erbium ion.

As organic host molecules usually have C-H bonds, quenching of the excited state of the lanthanide ion may occur by nearby C-H vibrational modes. It was found that the luminescence of the complexes according to the invention can be enhanced by partial deuteration of the host molecule. The present invention is also directed to optical amplifiers wherein the complex comprises a host molecule encapsulating the lanthanide ion, the host molecule being partially deuterated.

The invention also relates to novel electrically neutral lanthanide complexes that can be used with advantage in the polymeric optical waveguides described above. These complexes contain host molecules which readily complex with the lanthanide and encapsulate it in full. Such host molecules are formed by compounds found to have easy synthesis and satisfying the formula:

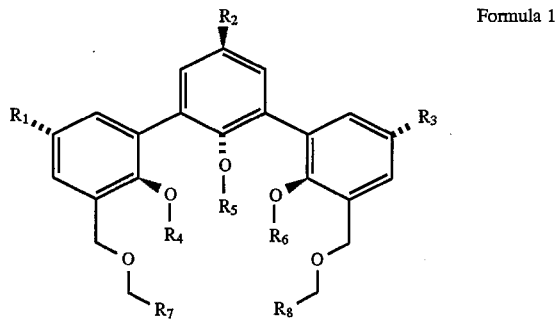

Formula 1 wherein $R_1$, $R_2$, $R_3$ may be the same or different and represent: —H, an alkyl group having 1–50 carbon atoms, an alkenyl group having 1–50 carbon atoms, a halogenated alkyl group having 1–50 carbon atoms, —C(O)H, —COOH, —O—$R_{10}$, —O—$R_{10}$—OH, —$R_{10}$—OH, —COO$R_{10}$, COO$R_{10}$—C(O)H, —COO$R_{10}$—COOH, O—$R_{10}$—NH$_2$, —$R_{10}$—NH$_2$, —NO$_2$, or an amine group;

$R_4$, $R_5$, $R_6$ may be the same or different and represent: —CH$_2$—(CH$_2$)$_x$COOH, —CD$_2$—(CH$_2$)$_x$COO H, —CH$_2$—(CH$_2$)$_x$COO$R_9$, —CD$_2$—(CH$_2$)$_x$COO$R_9$, —CH$_2$—(CH$_2$)$_x$SO$_3$H, —CH$_2$—(CH$_2$)$_x$SO$_3$R$_9$, —CD$_2$—(CH$_2$)$_x$SO$_3$R$_9$, —CH$_2$—(CH$_2$)$_x$—O—P(O)(OR$_9$)$_2$, —CD$_2$—(CH$_2$)$_x$—O—P(O)(OR$_9$)$_2$, —CH$_2$—(CH$_2$)$_x$—O—P(O)OH(OR$_9$), —CD$_2$—(CH$_2$)$_x$—O—P—(O)OH(OR$_9$), —CH$_2$—(CH$_2$)$_x$—O—P(OR$_9$)$_3$, —CD$_2$—(CH$_2$)$_x$—O—P(OR$_9$)$_3$, —CH$_2$—(CH$_2$)$_x$—O—POH(OR$_9$)$_2$, —CD$_2$—(CH$_2$)$_x$—O—POH(OR$_9$)$_2$, —CH$_2$—(CH$_2$)$_x$—O—P(O)H(OR$_9$), —CD$_2$—(CH$_2$)$_x$—O—P(O)HOR$_9$;

X is an integer from 0 to 3;

$R_7$, $R_8$ may be the same or different and represent: —C(O)—O—$R_{10}$, —C(O)—COOH, —CH(O)—COO$R_{10}$, —C(O)—NR$_{10}$R$_{10}$ may jointly, forming a cyclical compound, represent: —CH$_2$—O—(CH$_2$—CH$_2$—O—)$_n$—CH2—, —CH$_2$—O—(CD$_2$—CD$_2$—O)$_n$—CH$_2$—, —(CH$_2$—N(R$_{10}$)—CH$_2$)$_{n+1}$—, —CH$_2$—O—(CH$_2$—CH$_2$—N(R$_{10}$)—CH$_2$—CH$_2$—O)$_n$—CH$_2$—, —CH$_2$—O—(CD$_2$—CD$_2$—N(R$_{10}$)—CD$_2$—CD$_2$—O)$_n$—CH$_2$—, —C(O)—NR$_{10}$R$_{11}$—NR$_{10}$—C(O)—, —C(O)—O—R$_{11}$—O—C(O)$;

n is an integer from 0 to 3;

$R_9$ is a (deuterated) alkyl group having 1 to 3 carbon atoms or a phenyl group;

$R_{10}$ is a (deuterated) alkyl group or alkenyl group having 1 tot 50 carbon atoms;

$R_{11}$ is a (deuterated) alkyl group having 2 to 8 carbon atoms;

wherein the term alkyl group or alkenyl group refers to branched as well as linear groups.

These novel compounds belong to a group generally known as hemispherands. A major advantage of these novel hemispherands is that metal ions are incorporated by deprotonation of the acid groups. In the case of $R_4$, $R_5$ and/or $R_6$ representing ester groups, they may be deprotonated after saponification. The resulting tri-anion can form a neutral complex with a lanthanide$^{3+}$ ion. Thus a neutral complex is formed without a counterion being required as it is with conventional ligand complexes. Given that charged particles as a rule are objectionable in optical waveguides, where they may cause additional losses of signal, this is of importance. These hemispherands are eminantly suitable compounds for complexing with lanthanides, since they strip off all of the water on the lanthanide ion. Every lanthanide can be incorporated into these novel hemispherands according to formula 1. Praseodymium (Pt), neodymium (Nd), europium (Eu), terbium (Tb), erbium (Er), thullium (Tm), and ytterbium (Yb) are suitable for use in all of the above-described applications.

Lanthanide complexes, more particularly the above-described lanthanide/hemispherand complexes, can be dissolved, dispersed or covalently incorporated into the polymeric optical waveguide. It is possible in principle to utilise these complexes in all known optical waveguides. As was stated hereinbefore, the waveguides may be either in the form of fibres or flat.

Optical fibres usually have a core/cladding structure. The core consists of a transparent polymer traversed by the light beams. The cladding is also of a transparent polymer, but one with a lower index of refraction than the core's. Both the core and the cladding can be doped with lanthanides. The core and the cladding should meet the following requirements: firstly, of course, they have to be optically transparent. Further, the physical properties of the core and the cladding should be well matched (thermal coefficient of expansion, flexibility, optical properties, etc.). Also, the core and cladding material must adhere together satisfactorily. Needless to say, the core must be of a material with low optical signal loss. Finally, it is advantageous when the indices of refraction of the core and the cladding are easy to set. For a more detailed explanation about optical fibres reference is made to Kirk-Othmer's Encyclopedia of Chemical Technology, 3rd edition, Vol. 10, pp. 125–147.

Planar waveguides have a so-called sandwich structure, i.e., a layered structure in which a layer of transparent polymeric material is covered on either side with a layer of a transparent polymeric material having a lower index of refraction. Here again it is of importance that the various layers soundly adhere together, that the polymeric layers have matching physical properties, that material having low optical signal loss is used, and that the index of refraction is easy to set.

Examples of polymers which have little loss of signal include fluorinated and chlorinated polymers. As polymers suitable for use in optical applications may be mentioned: polyurethanes, polyesters, polycarbonates, polyimides, polyacrylates, and polymers derived from epoxides.

When the lanthanide complexes are incorporated into non-linear optical (NLO) polymers, the waveguides may be used as active units in optical circuits. For a more detailed explanation about the action of NLO polymers reference is made to C. B. McArdle (Loctite (Ireland) Ltd.), ed., Side Chain Liquid Crystal Polymers, Glasgow and London: Blackie, pp. 330–356. The combination of an amplifier and a circuit in a single waveguide makes it possible to have small-size intricate circuits. Also, loss of optical signal caused by switching on and off can be compensated for in this way. Special advantages can be gained by employing the novel neutral lanthanide complexes according to the present invention in NLO polymers. It is of importance not to have any charged particles in NLO optical waveguides. They give rise to drift during the waveguide's orientation and during switching, thus disturbing the switching action of the active unit. Using the electrically neutral lanthanide complexes according to the invention precludes the introduction of charged particles into the waveguide.

Alternatively, of course, lanthanide-doped NLO polymeric fibres can be employed solely as waveguide, without use being made of the non-linear optical properties of the polymer. Examples of NLO polymers that can be used include polyurethanes, polyesters, polycarbonates, polyimides, polyacrylates, and polymers derived from epoxides.

Figure 1:
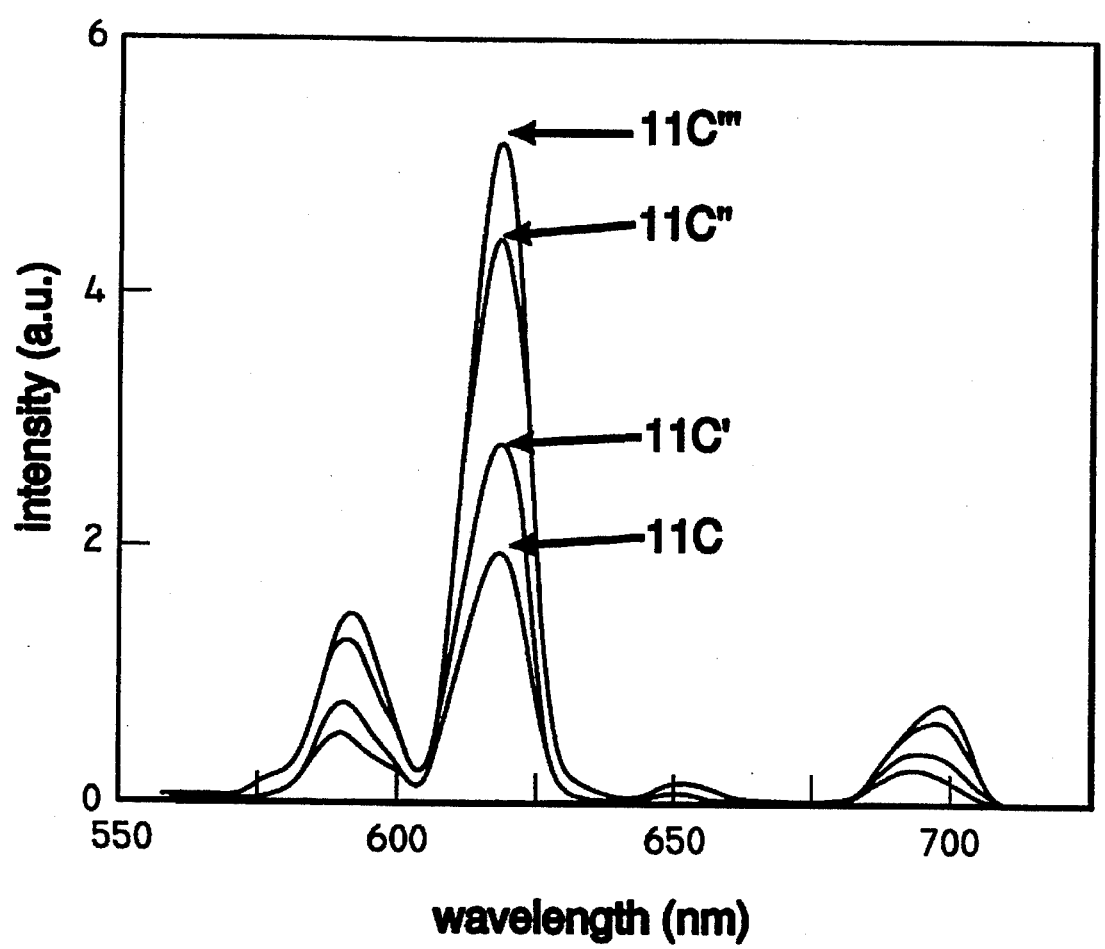
FIG. 1 shows the luminescence spectra of $10^{-4}$M solutions of $Eu^{3+}$ complexes in methanol-d, after exitation at 393 nrm.

The invention will be further illustrated with reference to several unlimitative examples.

DETAILED DESCRIPTION OF THE INVENTION

EXAMPLES

Synthesis of hemispherands according to formula 1: (For the formulae of the compounds and the reaction mechanisms readers are referred to the schedule.)

Compound 2

Compound 2 was synthesized in accordance with the procedure described by K. E. Koenig, G. M. Lein, P. Stucklet, T. Kaneda, and D. J. Cram, *J. Am. Chem. Soc.*, 101 (1979), 3553, use being made of p-cresol (compound 1).

Compound 3

A solution of compound 2 (20,0 g) and hexamethylene tetramine (26,3 g) in 150 ml of $CF_3COOH$ was heated to 90° C. for a period of 3,5 days. After cooling to 60°–70° C. 100 ml of water were added. After 2,5 hours of stirring the mixture was poured into 1 l of ethyl acetate and the acid was neutralised with a saturated solution of $NAHCO_3$ in water. The organic layer was isolated, washed once with brine, and then dried with $MgSO_4$. Following the removal of the salts by filtration the organic solvent was removed and the residue purified with the aid of column chromatography ($SiO_2$, $CH_2Cl_2$). The product was obtained as a yellow solid in 65% yield.

Compound 4

A mixture of compound 3 (14,3 g), allyl bromide (18,4 g), and $K_2CO_3$ (21,0 g) was heated, with refluxing, in 100 ml of $CH_3CN$ for 4 hours. After cooling down to room temperature the salts were filtered off and the filtrate was concentrated by evaporation. The resulting, virtually clear oil slowly solidified as it was left to stand. Compound 4 was obtained in nearly quantitative yield and did not undergo further purification.

Compound 5

To a solution of compound 4 (18,9 g) in a mixture of 100 ml of MeOH and 100 ml of THF was added $NaBH_4$ (1,45 g), with the temperature being kept below 20° C. The reaction mixture was poured into 400 ml of ethyl acetate and twice washed with brine. The organic layer was dried with $MgSO_4$, after which the salts were removed by filtration. The filtrate was condensed by evaporation and purified with the aid of column chromatography ($SiO_2$, ethyl acetate/ hexane (1:3)), after which compound 5 was obtained as a clear oil in 82% yield (based on compound 3).

Compound 6

To a solution of compound 5 (16,36 g) in 150 ml of dry toluene under an atmosphere of nitrogen $PBr_3$ (6,50 g) was added dropwise at room temperature. After 45 minutes 200 ml of ethyl acetate were added. The organic layer was washed with, successively, brine (2×), $NaHCO_{3aq}$ (1×), and brine (1×). After drying with $MgSO_4$, filtering off of the salts, and concentration by evaporation the residue was purified with the aid of column chromatography ($SiO_2$, $CH_2Cl_2$/hexane (1:2)). Compound 6 was obtained as a clear oil in 61% yield.

Compound 7a.$NaClO_4$

A solution of compound 6 (5,38 g, 8,59 mmoles) and diethylene glycol (0,91 g, 8,59 mmoles) in 100 ml of THF was added to a refluxing suspension of 4 mol. of NaH (0,83 g) in 400 ml of THF over a period of 10 hours. The reaction was performed under a dry nitrogen atmosphere. After the addition was completed the reaction mixture was refluxed for an additional 3 hours, after which it was cooled to room temperature. Subsequently, 10 ml of water were carefully added to neutralise the remaining NaH. After evaporation of the THF the residue was dissolved in a mixture of MeOH and $CH_2Cl_2$ (100 ml; 1:1) and 1 eq. of $NaClO_4.H_2O$ in 10 ml of MeOH was added. This mixture was concentrated to approximately 40 ml, after which an off-white precipitation was obtained. It was filtered off and washed once with MeOH to give 64% of compound 7a.$NaClO_4$.

Compound 7b

A solution of compound 6 (5,38 g, 8,59 mmoles) and the appropriate diol (2,35 g, 8,59 mmoles) in 100 ml of THF was added to a refluxing suspension of 4 mol. eq. of NaH (0,83 g) in 400 ml of THF over a period of 10 hours. The reaction was performed under a dry nitrogen atmosphere. After the addition 3 hours, after which it was cooled to room temperature.

Subsequently, 10 ml of water were carefully added to neutralise the remaining NaH. After evaporation of the AHF 300 ml of ethyl acetate were added. The organic layer was washed twice with brine, followed by drying with $MgSO_4$. The solvent was evaporated and the residue purified by column chromatography ($SiO_2$; ethyl acetate: N-hexane: 1:2) to give compound 7b as an oil in 55% yield.

Compound 7c

A solution of compound 6 (5,15 g, 8,23 mmoles) and the appropriate diol (2,94 g, 8,23 mmoles) in 100 ml of THF was added to a refluxing suspension of 4 mol. eq. of NaH (0,79 g) in 400 ml of THF over a period of 10 hours. The reaction was performed under a dry nitrogen atmosphere. After the addition was completed the reaction mixture was refluxed for an additional 3 hours, after which it was cooled to room temperature.

Subsequently, 10 ml of water were carefully added to neutralise the remaining NaH. After evaporation of the THF 300 ml of ethyl acetate were added. The organic layer was washed twice with brine, followed by drying with $MgSO_4$. The solvent was evaporated and the residue purified by column chromatography ($SiO_2$; ethyl acetate: n-hexane=2:5) to give compound 7c as an oil in 55% yield.

Compound 8a

A mixture of compound 7a.$NaClO_4$ (3,82 g, 3.98 mmoles), 5 mole % $Pd(OAc)_2$, 20 mole % $Ph_3P$, 3 mol. eq. of $Et_3N$, and 3 mol. eq. of HCOOH in 100 ml of EtOH and 20 ml of water was refluxed for one hours. The resulting mixture was cooled to 5° C. to give 8a as precipitation. It was filtered off and dried in a vacuum oven at 80° C. The crude product (90%) was almost pure on the NMR scale and was used without further treatment.

Compound 8b

A mixture of compound 7b (3,00 g, 4,07 mmoles), 5 mole % $Pd(OAc)_2$, 20 mole % $Ph_3P$, 3 mol. eq. of $Et_3N$, and 3 mol.

eq. of HCOOH in 50 ml of EtOH and 10 ml of water was refluxed for one hour. The resulting mixture was cooled to 10° C. to give 8b as precipitation. It was filtered off and dried in a vacuum oven at 80° C. The crude product (80%) was almost pure on the NMR scale and was used for further reactions without additional treatment. A sample was dissolved in $CH_2Cl_2$ and filtered over some silica gel. The silica gel was washed with some ethyl acetate and the combined organic layers were concentrated. The residue was dissolved in $CH_2Cl_2$ and boiled in the presence of activated carbon. After filtration the organic layer was concentrated and the off-white residue recrystallised from acetonitrile to give compound 8b as white powder.

Compound 8c

A mixture of compound 7c (3,61 g, 4,40 mmoles), 5 mole % Pd $(OAc)_2$, 20 mole % $pH_3P$, 3 mol. eq. of $Et_3N$, and 3 mol. eq. of HCOOH in 50 ml of EtOH and 10 ml of water was refluxed for one hour. The resulting mixture was cooled to 10° C. to give 8c as precipitation. It was filtered off and dried in a vacuum oven at 80° C. The crude product (93%) was almost pure on the NMR scale and was used for further reactions without additional treatment. A sample was dissolved in a mixture of ethyl acetate and $CH_2Cl_2$ and filtered over some silica gel. The silica gel was washed with with some ethyl acetate and the combined organic layers were concentrated. The off-white residue was recrystallised from acetonitrile to give compound 8c as white powder.

Compound 9a.$NaClO_4$

A mixture of compound 8a (1,00 g, 2,22 mmoles), ethyl bromoacetate (4 mol. eq.), and $K_2CO_3$ (4 mol. eq.) was refluxed in 50 ml of acetonitrile for 1,5 hours, after which it was cooled to room temperature. The salts were filtered off and washed once with acetonitrile. The combined organic layers were concentrated and the residue was dissolved in 10 ml of MeOH.

After the addition of 1 mol. eq. of $NaClO_4$ the solution was concentrated to about 3 ml to give 9a.$NaClO_4$ as off-white precipitation. It was filtered off and washed once to give the complex in 63% yield.

Compound 9b

A mixture of compound 8b (1,80 g, 2,92 mmoles), ethyl bromoacetate (10 mol. eq.), $NaClO_4.H_2O$ (15 mol. eq.), and $K_2CO_3$ (10 mol. eq.) was refluxed in 80 ml of acetonitrile for 10 hours, after which it was cooled to room temperature. The salts were filtered off and washed once with acetonitrile. The combined organic layers were concentrated to dryness and some $CH_2Cl_2$ was added. The resulting precipitation was filtered off and the filtrate was concentrated. The product was purified by column chromatography ($SiO_2$, ethyl acetate) to give compound 9b.$NaClO_4$ as an oil that still contained a little ethyl bromoacetate. The latter may be removed in the next step.

Compound 9c

A mixture of compound 8c (2,65 g, 3,78 mmoles), ethyl bromoacetate (10 mol. eq.), $NaClO_4.H_2O$ (15 mol. eq.) and $K_2CO_3$ (10 mol. eq.) was refluxed in 100 ml. of acetonitrile for 10 hours, after which it was cooled to room temperature. The salts were filtered off and washed once with acetonitrile. The combined organic layers were concentated to dryness and some $CH_2Cl_2$ was added. The resulting precipitation was filtered off and the filtrate concentrated. The product was purified by column chromatography ($SiO_2$, ethyl acetate) to give compound 9c.$NaClO_4$ as an oil that still contained a little ethyl bromoacetate. The latter may be removed in the next step.

Compound 10a

A mixture of compound 9a.$NaClO_4$ (0,30 g, 0,36 mmoles) in 5 ml of THF and 0,70 ml of 2,7M $Me_4N^+OH^-$ in water was stirred at room temperature for several hours until no starting material and only one new spot were present on TLC.

Subsequently, some water was added and acidified with 1M HCl solution to pH=1–2. The aqueous phase was extracted once with ethyl acetate. After drying with $MgSO_4$ the organic layer was concentrated to give compound 10a (90% yield) as a foam which was pure on the NMR scale.

Compound 10b

To a solution of compound 9b.$NaClO_4$ (2,45 g, 2,46 mmoles) in 30 ml of THF and 3 ml of water 13,2 ml of 2,7M $Me_4N^+OH^-$ in water were added and the resulting two-phase system was stirred for four days at room temperature.

Subsequently, 50 ml of water were added, followed by acidifying with 1M HCl solution to pH=1–2. The aqueous layer was extracted once with 150 ml of ethyl acetate. The organic layer was washed twice with brine and concentrated. The residue was stripped with toluene, after which it was dissolved in $CH_2Cl_2$ and filtered to give a lear solution. This was concentrated to give compound 10b as foam in 79% yield. It was pure on TLC and on the NMR scale.

Compound 10c

To a solution of 9c.$NaClO_4$ (2,97 g, 2,76 mmoles) in 30 ml of THF and 3 ml of water 14,8 ml of 2,7M $Me_4N^+OH^-$ in water were added and the resulting two-phase system was stirred for five days at room temperature. Subsequently, 50 ml of water were added, followed by acidifying with 1M HCl solution to pH=1–2. The aqueous layer was extracted once with 150 ml of ethyl acetate. The organic layer was washed twice with brine and concentrated. The residue was stripped with toluene, after which it wad dissolved in $CH_2Cl_2$ and filtered to give a clear solution. This was concentrated to give triacid 10c as foam in 88% yield. It was pure on TLC and on the NMR scale.

Incorporation of lanthanides in cyclic hemispherands (cf. schedule, compound 11)

General Procedure for Complexes 11b and 11c

To a solution of the triacid in MeOH (concentration 0,02–0,04M) three eq. of $Me_4N^+OH^-$ or $Et_3N$ were added. Directly after this addition a solution of $ErCl_3.6H_2O$, $EuCl_3.6H_2O$, $TbCl_3.6H_2O$, or $YCl_3.6H_2O$ in some MeOH (5–10 ml) was added. The resulting mixture was stirred for 10 minutes.

In the case of 11b, the formed precipitate was filtered off and washed twice with MeOH and dried in a vacuum oven (80° C.). In the case of 11c, the resulting milky mixture was concentrated to about 10 ml and 10–30 ml of water were added. The mixture was stirred for several minutes to give a very fine precipitate, which was filtered off and washed once with water. After drying under vacuum (80° C.) the complexes were obtained as microcrystalline powders.

Europium complex 11b (M=Eu)

The crude product was dissolved in warm DMSO and after the addition of some vol. eq. of $CH_3CN$ the complex precipitated overnight (36%). Mp 270° C. (decomposition). IR (KBr) 1659 and 1631 (C=O) $cm^{-1}$.

Terbium complex 11b (M=Tb)

The crude product was treated in the same way as the corresponding europium complex (27%). Mp 270° C. (decomposition).

Erbium complex 11b (M=Er)

No suitable solvent or mixture of solvents was found for the purification of the pale pink complex (87%). Mp 260° C. (decomposition).

Europium complex 11c (M=Eu)

The crude product was purified by treatment with boiling $CH_3CN$, after which the complex was obtained in 51% yield. Mp 230° C. (decomposition). IR (KBr) 1660 and 1630 (C=O) $cm^{-1}$.

Terbium complex 11c (M=Tb)

The crude product was purified by treatment with boiling $CH_3CN$, after which the complex was obtained in 53% yield. Mp 225° C. (decomposition).

Erbium complex 11c (M=Er)

The crude product was purified by treatment with boiling ethanol, giving the complex as a pale pink solid in 65% yield. Mp 240° C. (decomposition).

Deuterated complexes 11c', 11c", and 11c'"

Partially deuterated triacetates (11c', 11c", and 11c'") were obtained via the same synthesis route as described-above, using $(HO-CD_2-CD_2)_2-N$ and/or $BrCD_2COOMe$ as reagents. $(HO-CD_2-CD_2)_2-N$ was obtained in 70% yield by the alkylation in n-propanol of octadecylamine with ethylene oxide-$d_4$. The base catalysed hydrolysis of the triesters (9c) which contained deuterated arms, and the complexation reactions were carried out in methanol-$d_1$, in the presence of $D_2O$ to prevent the exchange of deuterium atoms by hodrogens.

Compound 12

A solution of compound 6 (6,24 g, 9,97 mmoles) and n-BuOCH$_2$CH$_2$OH (2,59 g, 21,95 mmoles) in dry THF was added to a stirred suspension of NaH (0,96 g, 40,0 mmoles) in 100 ml of THF, which was kept under a nitrogen atmosphere. The resulting mixture was refluxed for ½ hour and subsequently cooled to room temperature. The remaining NaH was neutralised by carefully adding 20 ml of water. After evaporation of the THF 200 ml of ethyl acetate were added. The organic layer was washed once with brine and dried with MgSO$_4$. The salts were filtered off and the filtrate was concentrated to give compound 12, which was used without further treatment.

Compound 13

A mixture of compound 12 (6,98 g, 9,97 mmoles9, Pd(OAc)$_2$ (0,09 g, 0,4 mmoles), Ph$_3$P (0,42 g, 0,16 mmoles), Et$_3$N (3,02 g, 29,91 mmoles), and HCOOH (1,38 g, 29,91 mmoles) was refluxed in a mixture of 100 ml of EtOH and 10 ml of water for 45 minutes. After cooling to room temperature the mixture was concentrated to about 10 ml and 200 ml of ethyl acetate were added. The organic layer was washed once with brine and dried with MgSO$_4$. The salts were filtered off and the filtrate was concentated. The residue was purified by column chromatography (SiO$_2$, ethyl acetate: n-hexane=1:3) to give compound 13 as a colourless oil in 53% yield from 6.

Compound 14

A mixture of compound 13 (3,00 g, 5,17 mmoles), ethyl bromoacetate (3,46 g, 20,69 mmoles), and K$_2$CO$_3$ (2,86 g, 20,69 mmoles) in 75 ml of acetonitrile was refluxed for 1,5 hours. After cooling to room temperature the salts were filtered off and the filtrate was concentrated. The residue was purified by column chromatography (SiO$_2$, ethyl acetate: n-hexane=1:2) to give compound 14 as a colourless oil in 82% yield.

Compound 15

Compound 14 (3,57 g, 4.26 mmoles) was hydrolysed in a mixture of 50 ml of MeOH and 15 ml of 15% NaOH$_{aq}$. After the reaction was completed according to TLC, 300 ml of water were added. The aqueous phase was acidified with 4M HCl$_{aq}$ to pH=1 followed by extraction with 100 ml of ethyl acetate. The organic layer was washed once with brine and dried with MgSO$_4$. After filtering off of the salts the filtrate was concentrated to give compound 15 as a colourless compound in quantitative yield.

Incorporation of lanthanides in acyclic hemispherand (cf. schedule, compound 16)

Compound 16

To a solution of compound 15 in MeOH 3 mol.eq. of 2,7M Me$_4$N$^+$OH$^-$ aq were added. To the resulting mixture a solution of 1 mol eq. of MCl$_3$.6H$_2$O (M=Eu, Tb, Er) or a solution of 1 mol eq. of Gd(NO$_3$)$_3$.5H$_2$O in MeOh was added. The organic solvent was removed and some water was added. In the case of M=Eu, Gd, and Tb the complex was extracted with CH$_2$Cl$_2$. The organic layer was dried with MgSO$_4$ and concentrated after filtering off of the salts. In the case of M=Er, the resulting pale pink complex was filtered off, washed once with water, and dried in a vacuum oven (80° C.).

Ad Eu:

The europium complex was obtained as a practically white solid (85%). A solution (CH$_2$Cl$_2$, MeOH, THF, etc.) of the europium complex displays red luminescence from excitation with UV light ($\lambda_{max}$=366 nanometers). This is also observed for the complex in the solid phase.

Ad Gd:

The gadolinium complex was purified by precipitation from a THF solution with the aid of n-hexane. The gadolinium complex was obtained as a white solid in a yield of 62%.

Ad Tb:

The terbium complex was purified by being boiled with acetone (31%). The terbium complex was obtained as a white solid in a yield of 31%. A solution (CH$_2$Cl$_2$, MeOH, THF, etc.) of the terbium complex displays green luminescence from excitation with UV light ($\lambda$=366 nanometers). This is also observed for the complex in the solid phase.

Ad Er:

The erbium complex was purified by being boiled with a mixture of MeOH and CH$_3$CN. The erbium complex was obtained as a pale pink solid in a yield of 40%.

SCHEDULE 1/3

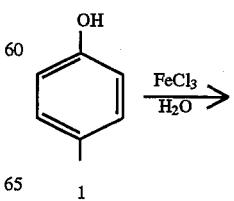

1

SCHEDULE 1/3
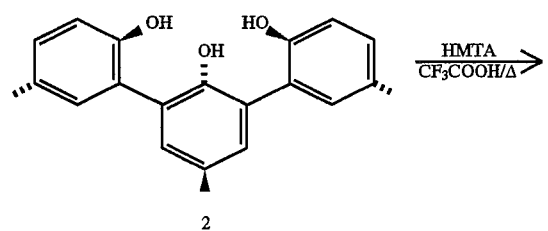
2
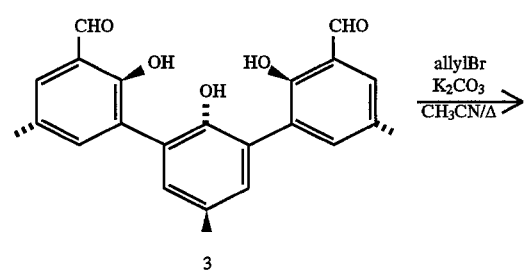
3
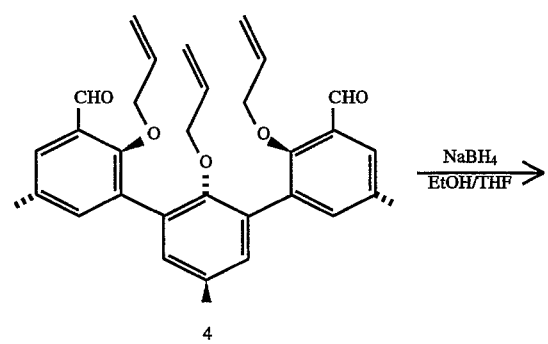
4
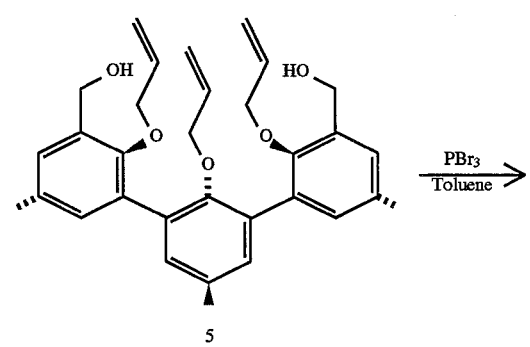
5
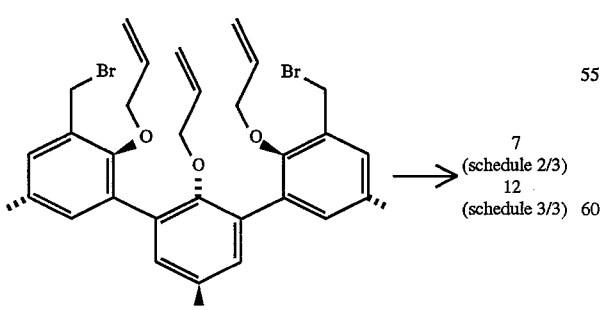
6 → 7 (schedule 2/3)
12 (schedule 3/3)
SCHEDULE 2/3
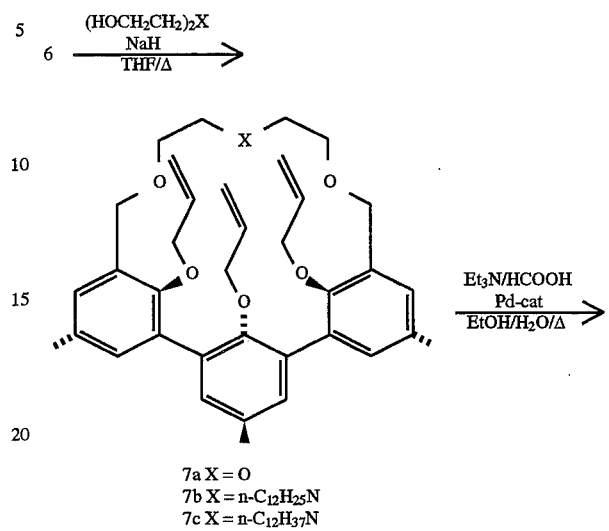
7a X = O
7b X = n-C$_{12}$H$_{25}$N
7c X = n-C$_{12}$H$_{37}$N
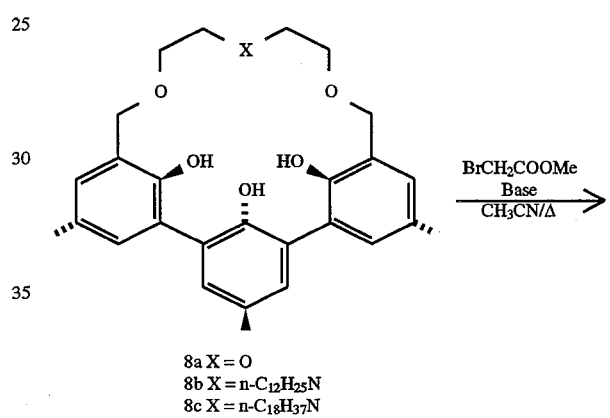
8a X = O
8b X = n-C$_{12}$H$_{25}$N
8c X = n-C$_{18}$H$_{37}$N
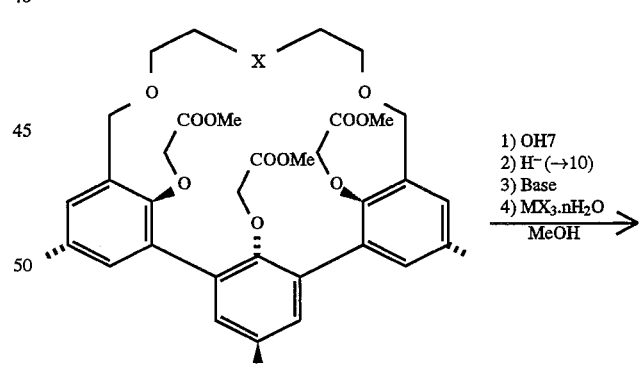
9a X = O
9b X = n-C$_{12}$H$_{25}$N
9c X = n-C$_{18}$H$_{37}$N

13
-continued
SCHEDULE 2/3

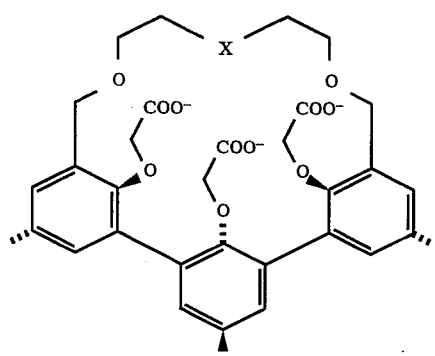

11a X = O
11b X = n-C₁₂H₂₅N
11c X = n-C₁₈H₃₇N

M = Eu, Tb, Er, Y

SCHEDULE 3/3

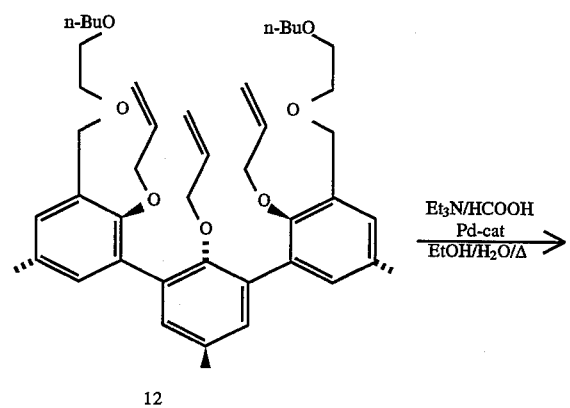

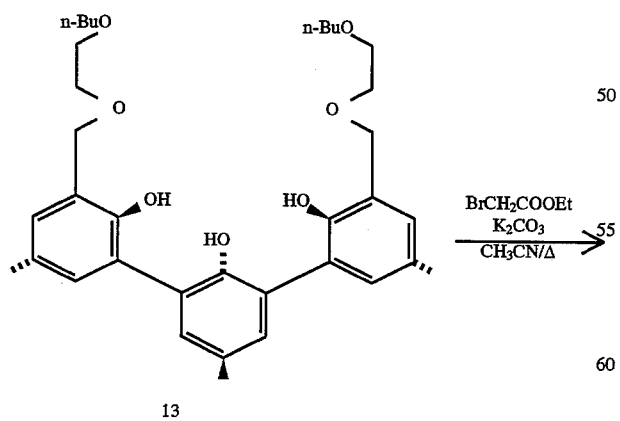

14
-continued
SCHEDULE 3/3

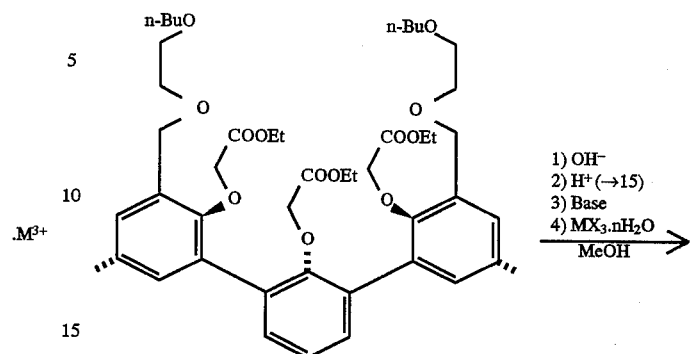

M = Gd, Eu, Er, Tb

Luminescence measurements were taken on both cyclic and acyclic hemispherand complexes. The lanthanide complexes were dried in a vacuum stove prior to use.

The luminescence measurements in the visible range were taken with a Spex® Fluorolog 2, with emission separation by a 0,22 mm single monochromator with a bandpass of 1,8 nm. Excitation was effected at 393 nm, 295 nm, and 266 nm. The excitation spectra were recorded with a monitoring wavelength of 614 nm for $Eu^{3+}$ and 544 nm for $Tb^{3+}$. A 0,22 mm double monochromator was used for excitation with a bandpass of 1,8 nm.

For the detection of the near infra-red luminescence two approaches were followed. In the first the 275 nm line of a Spectra Physics 2045® Ar laser was used for excitation. The CW output of the laser was modulated by a mechanical chopper at 75 Hz. The emission was detected by a Ge-diode and processed by a Satec Instruments® lock-in amplifier. The near-infrared luminescence was selected by means of a Si-wafer. In the second approach excitation was effected with a Spectra Physics® 3900 S Ti/sapphire lase at 980 nm. The laser light was modulated by a mechanical chopper at about 75 Hz. Emission was detected with a Ge-diode coupled to a lock-in amplifier. The emission light was separated with a 1,53±0,06 μm bandpass filter from Physical Optics Corporation®, i.e. optimized for $Er^{3+}$ luminescence.

Luminescence spectra were measured on $10^{-3}$M solutions of $EuCl_3$, acyclic, and cyclic Eu-complexes in methanol and in deuterated methanol. The integrated intensities of the 613 nm luminescence, the most intense peak in the Eu$^{3+}$ spectrum, are given in TABLE I, wherein $I_{MeOD}$ denotes the intensity in deuterated methanol, $I_{MeOH}$ denotes the intesity in methanol, and $I_{MeOD}/I_{MeOH}$ denotes the ratio of one to the other.

TABLE I

| Compound | Concentration (M) | λexc. (nm) | $I_{MeOD}$ (× 10⁴) | $I_{MeOH}$ (× 10⁴) | $I_{MeOD}/I_{MeOH}$ |
|---|---|---|---|---|---|
| EuCl$_3$ | 10$^{-3}$ | 393 | 87,5 | 7,4 | 11,8 |
|  |  | 295 | 68,6 | 6,6 | 10,4 |
|  |  | 266 | 67,3 | 5,7 | 11,8 |
| 16, M = Eu | 10$^{-3}$ | 393 | 62,8 | 14,6 | 4,3 |
|  |  | 295 | 313,4 | 86,8 | 3,6 |
|  |  | 266 | 47,1 | 11,3 | 4,2 |
| 11b, M = Eu | 10$^{-3}$ | 393 | 6,3 | 6,2 | 1,0 |
|  |  | 295 | 15,7 | 12,7 | 1,2 |
|  |  | 266 | — | — | — |

The results depicted in TABLE I show that the luminescence of EuCl$_3$ in deuterated methanol is much higher than in methanol. This illustrates the quenching by OH-groups of the excited state in EuCl$_3$. From the fact that the luminescence intensity is reduced much less in complexes according to the invention when using methanol instead of deuterated methanol, it can be concluded that the lanthanide ions are very well shielded by the hemispherand.

The luminescence spectra of 10$^{-4}$M solutions of Eu$^{3+}$ complexes (11c, 11c', 11c", and 11c''') in methanol-d, after excitation at 393 nm are depicted in FIG. 1. These spectra indicate that luminescence enhancement is obtained upon host molecule deuteration.

Further, luminescence emission and excitation spectra were measured on an acyclic Tb$^{3+}$ complex (compound 16) and an acyclic Eu$^{3+}$ complex (compound 16) in a thin film of PMMA. The luminescence spectra of both the Eu$^{3+}$ and the Tb$^{3+}$ complex in PMMA were exactly the same as those obtained in solution, which indicates that the same species are present in both matrices.

Luminescence emission and excitation spectra were measured of an acyclic Er$^{3+}$ complex (compound 16) in deuterated methanol. Both excitation at 275 nm and at 980 nm resulted in luminescence in the 1530 nm region.

We claim:

1. An optical amplifier doped with lanthanide ions, characterised in that the amplifier comprises a polymeric optical waveguide in which the lanthanide ion is present in the form of a complex.

2. An optical amplifier according to claim 1, characterised in that the lanthanide ion is an erbium ion, ytterbium ion, praseodymium ion, neodymium ion, europium ion, thulium ion and/or terbium ion.

3. An optical amplifier according to claim 2, characterised in that the amplifier comprises erbium ions and ytterbium ions.

4. An optical amplifier according to any one of the preceding claims, characterised in that the complex comprises a host molecule encapsulating the lanthanide ion, the host molecule being patrially deuterated.

5. An optical amplifier according to any one of claims 1–3, characterised in that the lanthanide ion is incorporated into a compound of the formula:

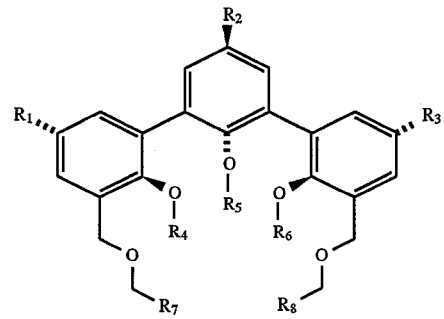

Formula 1 wherein $R_1$, $R_2$, $R_3$ may be the same or different and represent: —H, an alkyl group having 1 to 50 carbon atoms, an alkenyl group having 1 to 50 carbon atoms, a halogenated alkyl group having 1 to 50 carbon atoms, —C(O)H, —COOH, —O—R$_{10}$, —O—R$_{10}$—OH, —R$_{10}$—OH, —COOR$_{10}$, COOR$_{10}$—C(O)H, —COOR$_{10}$—COOH, O—R$_{10}$—NH$_2$, —R$_{10}$—NH$_2$, —NO$_2$ or an amine group;

$R_4$, $R_5$, $R_6$ may be the same or different and represent: —CH$_2$—(CH$_2$)$_x$COOH, —CD$_2$—(CH$_2$)$_x$COOH, —CH$_2$—(CH$_2$)$_x$COOR$_9$, —CD$_2$—(CH$_2$)$_x$COOR$_9$, —CH$_2$—(CH$_2$)$_x$SO$_3$H, —CH$_2$—(CH$_2$)$_x$SO$_3$R$_9$, —CD$_2$—(CH$_2$)$_x$SO$_3$R$_9$, —CH$_2$—(CH$_2$)$_x$—O—P(O)(OR$_9$)$_2$, —CD$_2$—(CH$_2$)$_x$—O—P(O)(OR$_9$)$_2$, —CH$_2$—(CH$_2$)$_x$—O—P(O)OH(OR$_9$), —CD$_2$—(CH$_2$)$_x$—O—P(O)OH(OR$_9$), —CH$_2$—(CH$_2$)$_x$—O—P(OR$_9$)$_3$, —CD$_2$—(CH$_2$)$_x$—O—P(OR$_9$)$_3$, —CH$_2$—(CH$_2$)$_x$—O—POH(OR$_9$)$_2$, —CD$_2$—(CH$_2$)$_x$—O—POH(OR$_9$)$_2$, —CH$_2$—(CH$_2$)$_x$—O—P(O)H(OR$_9$), —CD$_2$—(CH$_2$)$_x$—O—P(O)HOR$_9$;

x is an integer from 0 to 3;

$R_7$, $R_8$ may be the same or different and represent: —C(O)—O—R$_{10}$, —C(O)—COOH, —CH(O)—COOR$_{10}$, —C(O)—NR$_{10}$R$_{10}$ may jointly, forming a cyclical compound, represent: —CH$_2$—O—(CH$_2$—CH$_2$—O—)$_n$—CH2—, —CH$_2$—O—(CD$_2$—CD$_2$—O)$_n$—CH$_2$—, —(CH$_2$—N(R$_{10}$)—CH$_2$)$_{n+1}$—, —CH$_2$—O—(CH$_2$—CH$_2$—N(R$_{10}$)—CH$_2$—CH$_2$—O)$_n$—CH$_2$—, —CH$_2$—O—(CD$_2$—CD$_2$—N(R$_{10}$)—CD$_2$—CD$_2$—O)$_n$—CH$_2$—, —C(O)—NR$_{10}$R$_{11}$—NR$_{10}$—C(O)—, —C(O)—O—R$_{11}$—O—C(O);

n is an integer from 0 to 3;

$R_9$ is a (deuterated) alkyl group having 1 to 3 carbon atoms or a phenyl group;

$R_{10}$ is a (deuterated) alkyl group or alkenyl group having 1 to 50 carbon atoms;

$R_{11}$ is a (deuterated) alkyl group having 2 to 8 carbon atoms;

wherein the term alkyl group or alkenyl group refers to branched as well as linear groups.

6. An optical amplifier according to any one of claims 1–3, characterised in that the polymeric optical waveguide comprises a non-linear optical polymer.

7. A hemispherand, characterised in that it satisfies the formula:

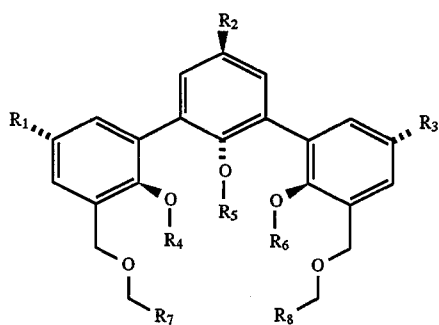

Formula 1 wherein $R_1$, $R_2$, $R_3$ may be the same or different and represent: —H, an alkyl group having 1 to 50 carbon atoms, an alkenyl group having 1 to 50 carbon atoms, a halogenated alkyl group having 1 to 50 carbon atoms, —C(O)H, —COOH, —O—$R_{10}$, —O—$R_{10}$—OH, —$R_{10}$—OH, —COOR$_{10}$, COOR$_{10}$—C(O)H, —COOR$_{10}$—COOH, O—$R_{10}$—NH$_2$, —$R_{10}$—NH$_2$, —NO$_2$ or an amine group;

$R_4$, $R_5$, $R_6$ may be the same or different and represent: —CH$_2$—(CH$_2$)$_x$COOH, —CD$_2$—(CH$_2$)$_x$COOH, —CH$_2$—(CH$_2$)$_x$COOR$_9$, —CD$_2$—(CH$_2$)$_x$COOR$_9$, —CH$_2$—(CH$_2$)$_x$SO$_3$H, —CH$_2$—(CH$_2$)$_x$SO$_3$R$_9$, —CD$_2$—(CH$_2$)$_x$SO$_3$R$_9$, —CH$_2$—(CH$_2$)$_x$—O—P(O)(OR$_9$)$_2$, —CD$_2$—(CH$_2$)$_x$—O—P(O)(OR$_9$)$_2$, —CH$_2$—(CH$_2$)$_x$—O—P(O)OH(OR$_9$), —CD$_2$—(CH$_2$)$_x$—O—P—(P)OH(OR$_9$), —CH$_2$—(CH$_2$)$_x$—O—P(OR$_9$)$_3$, —CD$_2$—(CH$_2$)$_x$—O—P(OR$_9$)$_3$, —CH$_2$—(CH$_2$)$_x$—O—POH(OR$_9$)$_2$, —CD$_2$—(CH$_2$)$_x$—O—POH(OR$_9$)$_2$, —CH$_2$—(CH$_2$)$_x$—O—P(O)H(OR$_9$), —CD$_2$—(CH$_2$)$_x$—O—P(O)HOR$_9$;

x is an integer from 0 to 3;

$R_7$, $R_8$ may be the same or different and represent: —C(O)—O—$R_{10}$, —C(O)—COOH, —CH(O)—COOR$_{10}$, —C(O)—NR$_{10}$R$_{10}$ may jointly, forming a cyclical compound, represent: —CH$_2$—O—(CH$_2$—CH$_2$—O—)$_n$—CH$_2$—, —CH$_2$—O—(CD$_2$—CD$_2$—O)$_n$—CH$_2$—, (CH$_2$—N (R$_{10}$)—CH$_2$)$_{n+1}$—, —CH$_2$—O—(CH$_2$—CH$_2$—N (R$_{10}$)—CH$_2$—CH$_2$—O)$_n$—CH$_2$—, —CH$_2$—O—(CD$_2$—CD$_2$—N (R$_{10}$)—CD$_2$—CD$_2$—O)$_n$—CH$_2$—, —C(O)—NR$_{10}$R$_{11}$—NR$_{10}$—C(O)—, —C(O)—O—R$_{11}$—O—C(O);

n is an integer from 0 to 3;

$R_9$ is a (deuterated) alkyl group having 1 to 3 carbon atoms or a phenyl group;

$R_{10}$ is a (deuterated) alkyl group or alkenyl group having 1 to 50 carbon atoms;

$R_{11}$ is a (deuterated) alkyl group having 2 to 8 carbon atoms;

wherein the term alkyl group or alkenyl group refers to branched as well as linear groups.

* * * * *